(12) United States Patent
De Mathelin et al.

(10) Patent No.: US 10,639,125 B2
(45) Date of Patent: May 5, 2020

(54) AUTOMATIC MULTIMODAL REAL-TIME TRACKING OF A MOVING MARKER FOR IMAGE PLANE ALIGNMENT INSIDE A MRI SCANNER

(71) Applicants: UNIVERSITE DE STRASBOURG (ETABLISSEMENT PUBLIC NATIONAL À CARACTÈRE SCIENTIFIQUE, CULTUREL ET PROFESSIONNEL, Strasbourg (FR); CENTRE NATIONAL DE LA RECHERCHE SCIENTIFIQUE (ETABLISSEMENT PUBLIC NATIONAL À CARACTÈRE SCIENTIFIQUE ET TECHNOLOGIQUE, Paris (FR); INSTITUT HOSPITALO-UNIVERSITAIRE DE CHIRURGIE MINI-INVASIVE GUIDEE PAR L'IMAGE (FONDATION DE COOPÉRATION SCIENTIFIQUE APPROUVÉE PAR DÉCRET MINISTÉRIEL DU 25 NOVEMBRE 2011 PUBLIÉ AU JOURNAL OFFICIEL DU 27 NOVEMBRE 2011, Strasbourg (FR)

(72) Inventors: Michel De Mathelin, Strasbourg (FR); Markus Neumann, Strasbourg (FR); Loic Cuvillon, Strasbourg (FR); Elodie Breton, Strasbourg (FR)

(73) Assignees: UNIVERSITE DE STRASBOURG (ETABLISSEMENT PUBLIC NATIONAL A CARACTERE SCIENTIFIQUE, CULTUREL ET PROFESSIONNEL), Strasbourg (FR); CENTRE NATIONAL DE LA RECHERCHE SCIENTIFIQUE (ETABLISSEMENT PUBLIC NATIONAL A CARACTERE SCIENTIFIQUE ET TECHNOLOGIQUE), Paris (FR); INSTITUT HOSPITALO-UNIVERSITAIRE DE CHIRURGIE MINI-INVASIVE GUIDEE PAR L'IMAGE (FONDATION DE COOPERATION SCIENTIFIQUE APPROUVEE PAR DECRET MINISTERIEL DU 25 NOVEMBRE 2011 PUBLIE AU JOURNAL OFFICIEL DU 27 NOVEMBRE 2011), Strasbourg (FR)

( * ) Notice: Subject to any disclaimer, the term of this patent is extended or adjusted under 35 U.S.C. 154(b) by 724 days.

(21) Appl. No.: 15/120,653

(22) PCT Filed: Feb. 24, 2015

(86) PCT No.: PCT/EP2015/053827
§ 371 (c)(1),
(2) Date: Aug. 22, 2016

(87) PCT Pub. No.: WO2015/124795
PCT Pub. Date: Aug. 27, 2015

(65) Prior Publication Data
US 2017/0014203 A1   Jan. 19, 2017

(30) Foreign Application Priority Data

Feb. 24, 2014   (EP) .................................... 14305255

(51) Int. Cl.
*A61B 90/00* (2016.01)
*G01R 33/28* (2006.01)
(Continued)

(52) U.S. Cl.
CPC ............ *A61B 90/39* (2016.02); *A61B 5/0035* (2013.01); *A61B 5/0077* (2013.01); *A61B 5/055* (2013.01);
(Continued)

(58) Field of Classification Search
CPC .... A61B 2090/3995; A61B 2034/2055; A61B 90/39; A61B 90/13; A61B 5/1127;
(Continued)

(56) References Cited

U.S. PATENT DOCUMENTS

| | | | | |
|---|---|---|---|---|
| 5,545,993 | A * | 8/1996 | Taguchi | G01R 33/5676 324/307 |
| 6,026,315 | A * | 2/2000 | Lenz | G01R 33/285 600/411 |

(Continued)

FOREIGN PATENT DOCUMENTS

| | | |
|---|---|---|
| EP | 1 524 626 A2 | 4/2005 |
| WO | 2011/027942 A1 | 3/2011 |

OTHER PUBLICATIONS

International Search Report, dated May 21, 2015, from corresponding PCT Application.

*Primary Examiner* — Bill Thomson
*Assistant Examiner* — Aminah Asghar
(74) *Attorney, Agent, or Firm* — Young & Thompson

(57) ABSTRACT

A system for an automatic multimodal real-time tracking of moving instruments for image plane alignment inside an MRI scanner includes:
- an MRI scanner,
- an MRI multi-plane pulse sequence generating unit allowing to interactively modify the position and orientation of one or several image planes in real-time,
- one or several external optical sensors with high frame rate, preferably a RGB-D sensor or other similar camera system like a stereovision systems,
- a multimodal marker including at least one MR visible feature and one visual feature able to be tracked by both the MRI scanner and the at least one external optical sensor,
- a computer for processing in real-time images from both MRI and optical sensor to fuse the detected marker position and orientation or pose from both modalities, and predict the next image plane position and orientation based on the estimated motion of the moving marker.

17 Claims, 6 Drawing Sheets

(51) Int. Cl.

| | |
|---|---|
| *A61B 5/00* | (2006.01) |
| *A61B 5/055* | (2006.01) |
| *A61B 5/06* | (2006.01) |
| *A61B 5/11* | (2006.01) |
| *A61B 34/20* | (2016.01) |
| *A61B 90/13* | (2016.01) |

(52) U.S. Cl.
CPC .............. *A61B 5/065* (2013.01); *A61B 5/066* (2013.01); *A61B 5/1127* (2013.01); *A61B 90/13* (2016.02); *G01R 33/283* (2013.01); *G01R 33/287* (2013.01); *A61B 2034/2051* (2016.02); *A61B 2034/2055* (2016.02); *A61B 2034/2057* (2016.02); *A61B 2034/2065* (2016.02); *A61B 2034/2072* (2016.02); *A61B 2090/364* (2016.02); *A61B 2090/3937* (2016.02); *A61B 2090/3954* (2016.02); *A61B 2090/3995* (2016.02); *G01R 33/285* (2013.01)

(58) Field of Classification Search
CPC ....... A61B 5/066; A61B 5/0077; A61B 5/055; A61B 5/065; A61B 5/0035; A61B 2034/2051; A61B 2090/364; A61B 2034/2072; A61B 2034/2065; A61B 2034/2057; A61B 2090/3937; A61B 2090/3954; G01R 33/287; G01R 33/283; G01R 33/285
USPC .................................................. 600/410–423
See application file for complete search history.

(56) References Cited

U.S. PATENT DOCUMENTS

| | | | | |
|---|---|---|---|---|
| 6,167,295 | A * | 12/2000 | Cosman | A61B 90/10 600/414 |
| 6,516,213 | B1 | 2/2003 | Nevo | |
| 8,374,411 | B2 | 2/2013 | Ernst et al. | |
| 2001/0009853 | A1 | 7/2001 | Arimitsu | |
| 2004/0171927 | A1 * | 9/2004 | Lowen | A61B 5/055 600/410 |
| 2005/0054910 | A1 * | 3/2005 | Tremblay | A61B 5/055 600/411 |
| 2005/0054913 | A1 | 3/2005 | Duerk et al. | |
| 2005/0137475 | A1 * | 6/2005 | Dold | A61B 5/055 600/414 |
| 2006/0258938 | A1 * | 11/2006 | Hoffman | A61B 1/00193 600/424 |
| 2007/0253599 | A1 * | 11/2007 | White | G01R 33/56509 382/107 |
| 2007/0280508 | A1 * | 12/2007 | Ernst | A61B 5/055 382/107 |
| 2009/0209846 | A1 * | 8/2009 | Bammer | A61B 5/055 600/421 |
| 2010/0280353 | A1 | 11/2010 | Roth et al. | |
| 2010/0331855 | A1 * | 12/2010 | Zhao | A61B 34/30 606/130 |
| 2011/0098553 | A1 | 4/2011 | Robbins et al. | |
| 2014/0031668 | A1 * | 1/2014 | Mobasser | A61B 5/062 600/409 |
| 2015/0057526 | A1 * | 2/2015 | Gerken | A61B 6/54 600/411 |
| 2016/0262663 | A1 * | 9/2016 | Maclaren | A61B 5/0555 |

* cited by examiner

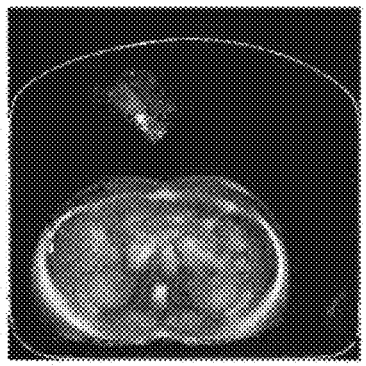
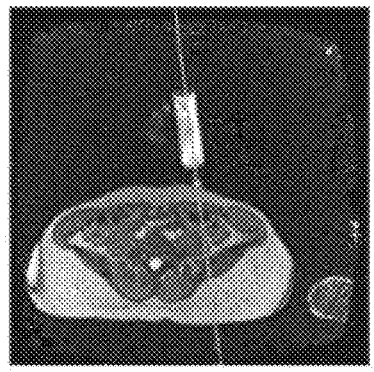
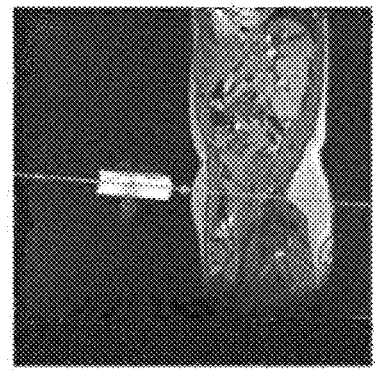
FIG. 6a         FIG. 6b         FIG. 6c
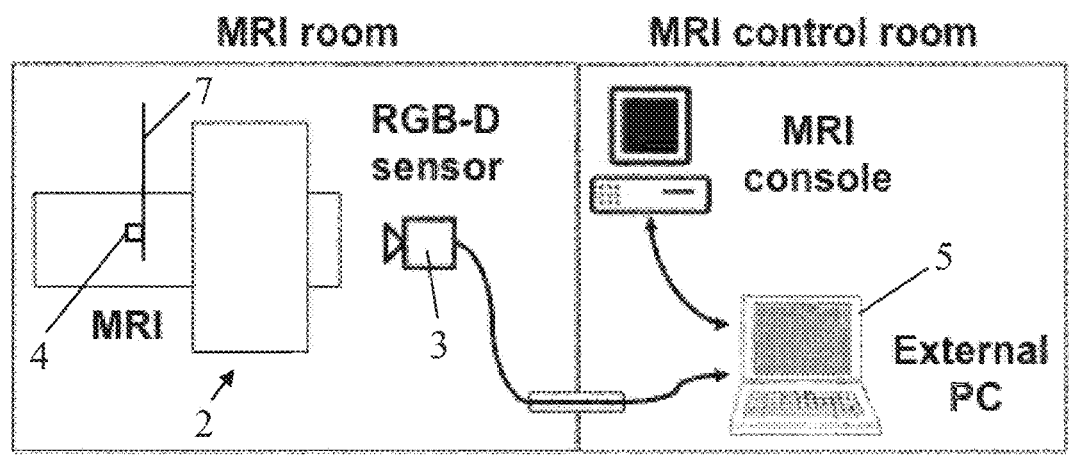
FIG. 7

AUTOMATIC MULTIMODAL REAL-TIME TRACKING OF A MOVING MARKER FOR IMAGE PLANE ALIGNMENT INSIDE A MRI SCANNER

The invention relates to the field of image guided monitoring, diagnostic procedures and therapies and more specifically to the tracking of a mobile marker, stand-alone or associated with a holding system or a moving instrument, detectable with several position sensors, for automatic alignment of the image planes.

The invention concerns more specifically a system and a method for automatic multimodal real-time tracking of a mobile marker, stand-alone or associated with a holding system or a moving instrument for image plane alignment inside a Magnetic Resonance Imaging scanner.

In the following description, a marker is a feature or device that can be detected with a specific sensor modality (e.g. medical imaging scanner, or camera) based on its color, material, shape, configuration or other measurable signal (e.g. magnetic field). A multimodal marker is a marker which can be detected in at least two different kinds of sensors.

In the following, mobile or moving in relation to a marker, a holding system or an instrument means that the concerned item can move in relation to a fixed or stationary frame (for example the MRI scanner frame) through the motion or movement imposed by the body or item it is rigidly associated with (skin of a subject, holding system, instrument), said movement being a voluntary or controlled movement (practitioner, patient, holder arm) or an unvoluntary or physiological movement (physiological movement of the subject such as respiratory movement).

In the following description, an instrument can be any non-invasive passive or active device, as well as a medical instrument, such as a biopsy needle or thermal therapy probe.

One of the major but not limitative scope of application of the present invention is the field of interventional radiology.

Interventional radiology consists in using medical imaging for the guidance of minimally invasive surgical procedures. Typical procedures such as biopsies, infiltrations or ablations of tumors can be performed for diagnostic or therapeutic reasons. They are performed through percutaneous access and are directly monitored through a medical imaging device. The used medical imaging modalities include ultrasound (US), computer tomography (CT) or magnetic resonance imaging (MRI). Advantages of MRI-guidance for interventional radiology include absence of ionizing radiation exposure for both patient and medical staff, intrinsic soft tissue contrast and free image plane orientation and positioning The possibility to image any plane orientation and position is a strong advantage of MRI-guidance, but it also often results in MR-guided procedures to be time consuming. One or several successive image planes are continuously acquired to monitor the procedure in real-time. Real-time acquisition pulse sequences offer the possibility to interactively modify the position and orientation of image planes during the procedure. Typically, physicians are interested in the image planes aligned to the main axis of the interventional instrument to obtain a "3D-like" vision of the instrument, target lesion and the surrounding anatomical structures of interest. As the physician is occupied with the surgical procedure, he/she cannot at the same time align the image planes for optimal position and orientation, given the instrument motion.

In order to monitor the advancement of the instrument towards the target area inside the patient's body, a technologist or technician at the MRI console thus manually aligns the image planes along the interventional instrument axis, or to any image plane of interest for the physician to accurately visualize the surrounding anatomy.

As a consequence, the quality and delay of the optimal positioning and alignment of the image planes strongly depends on the experience of the technologist or technician at the MRI console, on his/her communication means with the physician and on the experience of them together as a team. Therefore, automatic solutions, not requiring the action of the technologist, are expected to accelerate and improve the accuracy of the image plane alignment to the moving instrument or any other feature.

At the beginning of the interventional procedure, the physician searches for the optimal interventional instrument paths from the entry point on the patient's skin towards the targeted lesion or tissue region inside the patient's body. The instrument path is chosen to minimize the vicinity of anatomical sensitive structures that could be harmed by the instrument. Typically, the entry point and angulation are interactively searched with the physician using his/her finger or a syringe filled with an MR visible solution, while the technologist aligns the image planes with respect to the finger/syringe main axis. The physician moves the finger/syringe, while the technologist or technician tries to remain aligned with its main axis, until the physician makes the decision for the optimal instrument path, based on the real-time images aligned to the finger/syringe. Given the manual tracking of the finger/syringe, this process can be time consuming and is expected to benefit from an automatic tracking system.

Both passive and active solutions have been proposed for automatic alignment of the MR image planes to moving interventional instruments.

Systems not requiring additional electronic hardware beside the MRI scanner are herein considered passive. In "Automatic passive tracking of an endorectal prostate biopsy device using phase-only cross-correlation". A. de Oliveira, J. Rauschenberg, D. Beyersdorff, W. Semmler and M. Bock. Magnetic Resonance in Medicine, 59(5):1043-1050, 2008, a commercially available prostate biopsy passive marker (PBPM) is used for implementation of an automatic image plane alignment workflow. The PBPM is a contrast agent-filled hollow cylinder through which the needle is passed. Two tracking-dedicated image planes orthogonal to the main axis of the PBPM are acquired. The ring shaped PBPM is then detected through phase-only cross-correlation on both image planes in order to align a third clinical image plane to the needle axis.

The advantage of this technique is its simplicity, as it is based on a commercially available passive marker and does not require additional sensor besides the MRI scanner. Such solution is also inherently wireless. The main drawback of this technique is that two dedicated tracking images have to be acquired for each clinical image plane alignment, therefore reducing the clinical image acquisition rate. In addition, the tracking speed is limited by the MRI frame rate acquisition. Moreover, the tracking has to be manually initiated by defining two image planes crossing the marker axis.

On the other hand, active tracking systems—i.e. using additional electronic hardware—do not rely on the MRI image acquisition for marker detection.

Spatially varying transient magnetic field gradients are used in MRI for spatial encoding. These magnetic field gradients can be used in order to determine the position and orientation inside the MRI scanner of one or several magnetic field sensors, that can also be attached to a surgical device. For that purpose, either the magnetic field gradients applied for imaging can be directly measured during the image acquisition, or additional gradients can be specifically played and measured for tracking.

One possibility for magnetic field gradient measurement is the use of radio-frequency (RF) pick up coils measuring induced voltages during gradient switching The EndoScout® system of Robin Medical, Baltimore, Md. (see also US 2010/0280353 A1, U.S. Pat. No. 6,516,213 B1) is a commercially available device using three orthogonal RF pick up coils for tracking of interventional instruments. Voltages induced in the RF picking coil are measured and compared to a gradient map for determination of the position and orientation of the sensor inside the MRI scanner.

Small tracking and RF coils can be integrated in interventional devices and can be used for detection and tracking applications. These RF coils are directly connected to the receiver system of the MRI scanner, similar to imaging receiver RF coils. Their detection is realized with dedicated RF pulses and magnetic field gradients that are interleaved with the imaging phases of an MRI pulse sequence. In "MR-guided intravascular procedures: Real-time parameter control and automated slice positioning with active tracking coils". M. Bock, S. Volz, S. Zühlsdorff, R. Umathum, C. Fink, P. Hallscheidt and W. Semmler. Journal of Magnetic Resonance Imaging, 19(5):580-589, 2004, a catheter with three integrated receiver RF coils is presented in combination with dedicated real-time pulse sequence, user interface and signal post-processing allowing the automatic alignment of the acquired image planes according to the performed actual catheter position and orientation.

Such a system using two RF coils is described in US 2005/054913 to adapt in real time one or more MRI acquisition parameters, including the position and orientation of the image plane. The update of the selected parameters is based on the estimation of the velocity of the tracking RF coils from a set of MR acquisitions. As mentioned earlier, dedicated MR images and pulse sequences (i.e. in this patent 1D projection) are required to determine the positions of RF coils, and subsequently their velocities.

Advantages of magnetic field gradient-based tracking are their high spatial accuracy and their independence from MR image contrast. Their drawbacks are the need for additional and often costly hardware that must be compatible with the specific MRI set-up and pulse sequences.

Optical tracking systems use optical cameras and markers for tracking of rigid percutaneous interventional instruments used for biopsies, ablations and infiltrations. In "Needle positioning in interventional MRI procedure: real time optical localisation and accordance with the roadmap". R. Viard, N. Betrouni, J. Rousseau, S. Mordon, 0. Ernst and S. Maouche. In Engineering in Medicine and Biology Society, 2007. EMBS 2007. 29th Annual International Conference of the IEEE, pages 2748-2751, 2007, a stereoscopic camera system consisting in four CCD monochromic cameras is used for detection of an infrared LED attached to the distal end of a needle inside a C-arm MRI scanner.

The presented system also provides a laser pointer for indication of the planned needle insertion point on the patient's skin.

In "MRI-guided trephine biopsy and fine-needle aspiration in the diagnosis of bone lesions in low-field (0.23 T) MRI system using optical instrument tracking". R. Blanco Sequeiros, R. Klemola, R. Ojala, L. Jyrkinen, E. Lappi-Blanco, Y. Soini and O. Tervonen. European Radiology, 12(4):830-835, April 2002, a similar system using only one camera and several markers attached to the biopsy instrument and the MRI scanner is presented.

The main advantage of optical tracking systems is that no MRI pulse sequence alteration is necessary as the optical system is totally independent from the MRI technology. Optical tracking systems also have a high spatial and temporal accuracy for tracking optical markers placed on the outer part of surgical instruments that remain outside the patient body. Their drawbacks are the need for a line-of-sight link between optical marker and camera, and thus their limited usability for closed-bore scanners. For the same reason, only the outer part of the medical instrument, remaining outside of the patient body, can be optically tracked. Furthermore a registration step is necessary between the camera coordinate system and the MRI scanner coordinate system. The registration step is typically performed before the procedure, and must be repeated if the optical sensor is moved (or re-oriented) relative to the medical imaging scanner.

Neither active nor passive approaches are fully optimal solutions for tracking of moving instruments equipped with markers or more generally mobile markers as such, in order to automatically align the MR image planes.

The main drawback of the purely MR image based approach is the coupling of the tracking speed to the slow (on the order of 1 image/s) image acquisition rate of the clinical MRI sequence. Also the marker can lay outside the acquired image plane, either outside of the image field-of-view or outside of the acquired image thickness, so that the marker is no longer, or only partially, visible in the MR images. Therefore the marker cannot be detected in the MR image which impedes its tracking.

The inherent drawback of optical sensor based approaches is the need for an unobstructed line-of-sight between the optical sensor and the tracking marker. Moreover, an accurate a priori registration of the optical sensor frame with respect to the MRI scanner system is needed. In case the optical sensor position or orientation relative to the MR scanner is altered, the registration step must be renewed.

EP 1,524,626 A2 describes an optical-based tracking with a marker both detected in MR images and in the optical sensor images. Nevertheless, a prior registration of the system with the MRI system is required, and no solution to a loss of the line-of-sight link in the constrained scanner in-bore space is considered. No model of motion or fusion between MRI tracking and optical-based systems is proposed: the tracking is achieved based on optical sensor data alone.

US 2001/09853 describes an automatic registration between MR images and an image guidance system. The image guidance system is composed of a set of cameras that tracks in real-time a surgical tool and displays on a screen its 3D position with respect to previously acquired MR images. The automatic registration between the tool and the MR image is possible thanks to a marker fixed on the patient with some features only MR visible and other only visible by the image guidance system. The procedure is here conducted outside the MR imaging system and there is no real-time MRI guidance with MRI fluoroscopic images dynamically aligned to the surgical tool (which is not designed to be visible in the MR scanner). Control and guidance of MR images are only periodically acquired, and with interruption of the procedure. These MR images are manually positioned. Displacement of organs subject to respiratory motion or tissue damages due to the surgical tool can not be assessed in real-time.

In U.S. Pat. No. 8,374,411 B2, an optical tracker is used for motion compensation during the MR image acquisition in order to avoid motion blur in the reconstructed MR image. Also, in WO 2011/27942, the reconstructed MR images are further refined by taking into account both the blur, but also the spatial modification of the magnetic susceptibility distribution induced by the motion of the anatomical structures. Estimation of the motion is based on optical tracking with a camera and its dedicated markers are positioned on the patient. These target applications, i.e. motion compensation in the reconstructed images, differ from MR image plane alignment as described hereinafter. In addition, the used marker is only detected by the optical tracker and is not visible in the MR images. Furthermore, object tracking relies exclusively on the optical marker and sensor, so that no solution is proposed for a loss of the line-of-sight between optical marker and optical sensor.

It is an aim of the invention to overcome at least the main drawbacks of the existing solutions exposed hereinbefore, and preferably also to meet the aforementioned needs.

There is also a need in the context of MRI imaging for performing a physically guided scanning of the anatomy of a subject and for patient motion tracking in view of stabilized image acquisition.

To that end, the invention proposes a system for tracking a moving marker, stand-alone or fixed on an instrument, a holding system or a body of a subject, comprising:
  an MRI scanner,
  an MRI multi-plane pulse sequence generating means allowing to interactively modify the position and orientation of one or several image planes in real-time,
  one or several external optical sensors with high frame rate, preferably a RGB-D sensor or an other similar camera system like a stereovision systems,
  a multimodal marker comprising at least one MR visible feature and one visual feature able to be tracked by both the MRI scanner and the at least one external optical sensor,
  a computer able to process in real-time the images from both MRI and optical sensor in order to fuse the detected marker position and orientation or pose from both modalities, and predict or estimate the next image plane position and orientation based on the estimated motion of the moving marker, in order to automatically track said marker and automatically align the image planes with respect to the marker, or to a system or body location this latter is fixed on.

Possible additional features of the inventive system are mentioned hereinafter in the specification, as well as in the dependant claims, in particular in view of the used marker and the fusion algorithm.

The invention also concerns a method for tracking a moving marker, stand-alone or possibly fixed on an instrument, on a holding system or on a patient's body, wherein said method comprises an automatic image plane alignment process using the system as described before, said process comprising the steps of processing in real-time the images from both MRI and optical sensor in order to fuse the detected marker position and orientation or pose from both modalities, and of predicting or estimating the next image plane position and orientation based on the estimated motion of the moving marker, in order to automatically track said marker and automatically align the image planes with respect to the marker, or to the instrument system or body location it is fixed on.

Finally, the invention also encompasses a method for scanning the anatomy of a subject, an image guided medical intervention method and a method for tracking subject motion during MR imaging, based on, making use of and/or incorporating the aforementioned tracking method and making use of the claimed system.

The main idea of the invention is to propose a hybrid workflow for automatic scan plane alignment to a moving or mobile device, consisting of or associated with a marker, said workflow combining a passive tracking approach, of (for example a contrast-agent filled) marker in the MR image, with an active tracking approach, based on measurements of an optical sensor or a similar tracking means.

The used marker device combines at least one MR visible feature and at least one visual feature in order to be independently tracked by both the MRI scanner and the optical sensor.

Combination of both tracking approaches enables to combine their respective advantages in order to compensate for their individual drawbacks. In a preferred embodiment, the optical sensor is a RGB-D sensor. The hybrid tracking approach can use an Information Filter in order to fuse the pose measurements from both sensors, each having its own sampling rate. The pose of the marker can be estimated and fed to the Information Filter which returns the prediction for the pose of the next MR image acquisition. The inventive hybrid tracking approach allows both to use the MRI and the optical sensor in combination, or as stand-alone tracking modalities when the other measurement is unavailable, by fusing their measurements through use of an Information filter.

Simultaneous measurements in both modalities enable the online auto-registration of the system, suppressing the need for any time-consuming prior registration of the optical sensor spatial coordinate system with regard to the MRI frame.

As for the advantageous effects of the invention, one can notice that the MRI feature detection has the strong advantage of providing an inherent spatial location in the MRI spatial coordinate system. Main advantages of the optical feature tracking are its independence from the MRI acquisition, and its high temporal sampling rate compared to the MRI acquisition rate. The hybrid solution of the invention cumulates these advantages.

In case of loss of the line-of-sight between the marker and the optical sensor, the tracking and plane alignment is ensured by the passive feature tracking in the MR images alone, through the use of an information filter. Similarly, in case of detection failure of the passive feature tracking in the MR images, the information filter allows for the optical tracking alone to ensure the automatic tracking of the moving instrument.

Moreover, in case the vision sensor location (or orientation) inside the MRI room is changed during the procedure, for instance to achieve an unobstructed line-of-sight between the optical sensor and the optical marker, the registration of the system is online and automatic, exactly in the same manner as the initial registration.

The man skilled in the art will understand that the inventive method may be used for the automatic registration of any tracking system to the MRI spatial coordinate system.

The present invention will be better understood thanks to the following description and drawings of different embodiments of said invention given as non limitative examples thereof.

In the accompanying drawings:

FIGS. 6a to 6c are MR images of the marker during its pose tracking. FIGS. 6b and 6c are respectively sagittal and transversal plane images with an overlay depicting results of the marker position and orientation detection;

Figure 1:
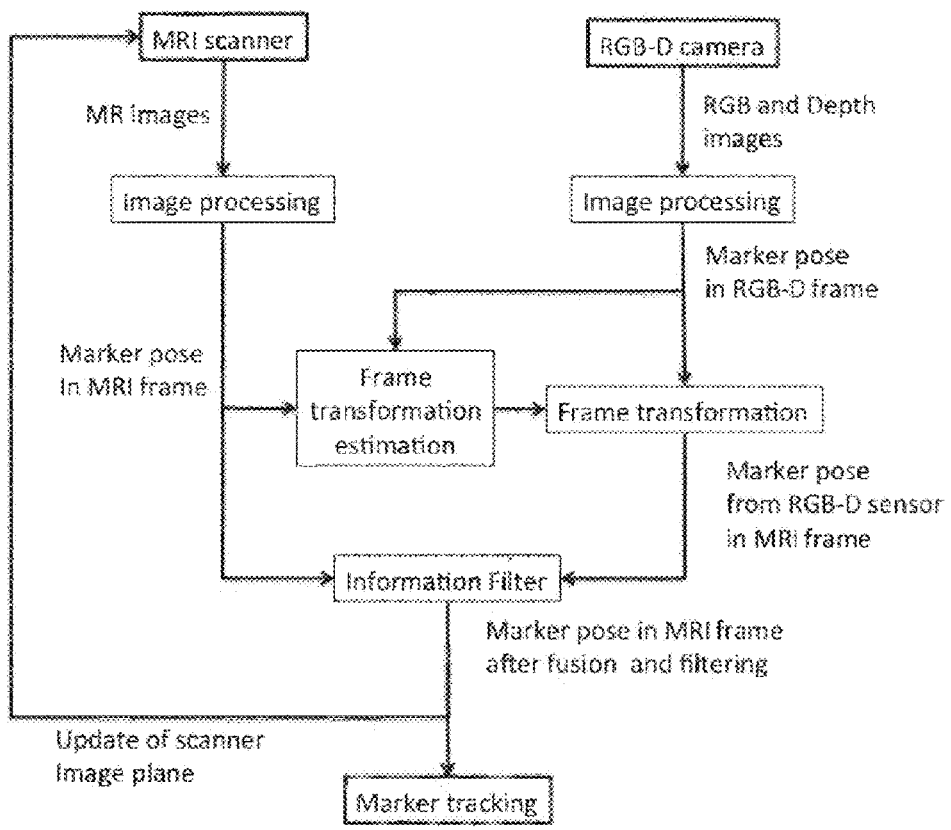
FIG. 1 is a flow chart of the multimodal automatic tracking and online registration process in a preferred embodiment with RGB-D sensor as external optical sensor.
Figure 2:
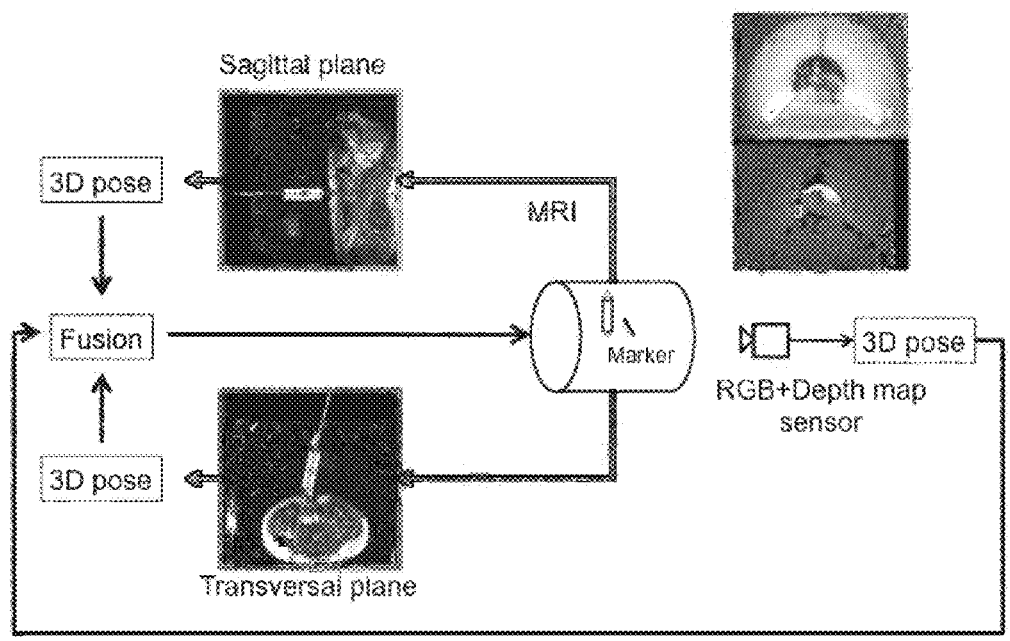
FIG. 2 is a flow chart of the real-time automatic multimodal tracking, showing typical MR images with the preferred embodiment.
Figure 8:
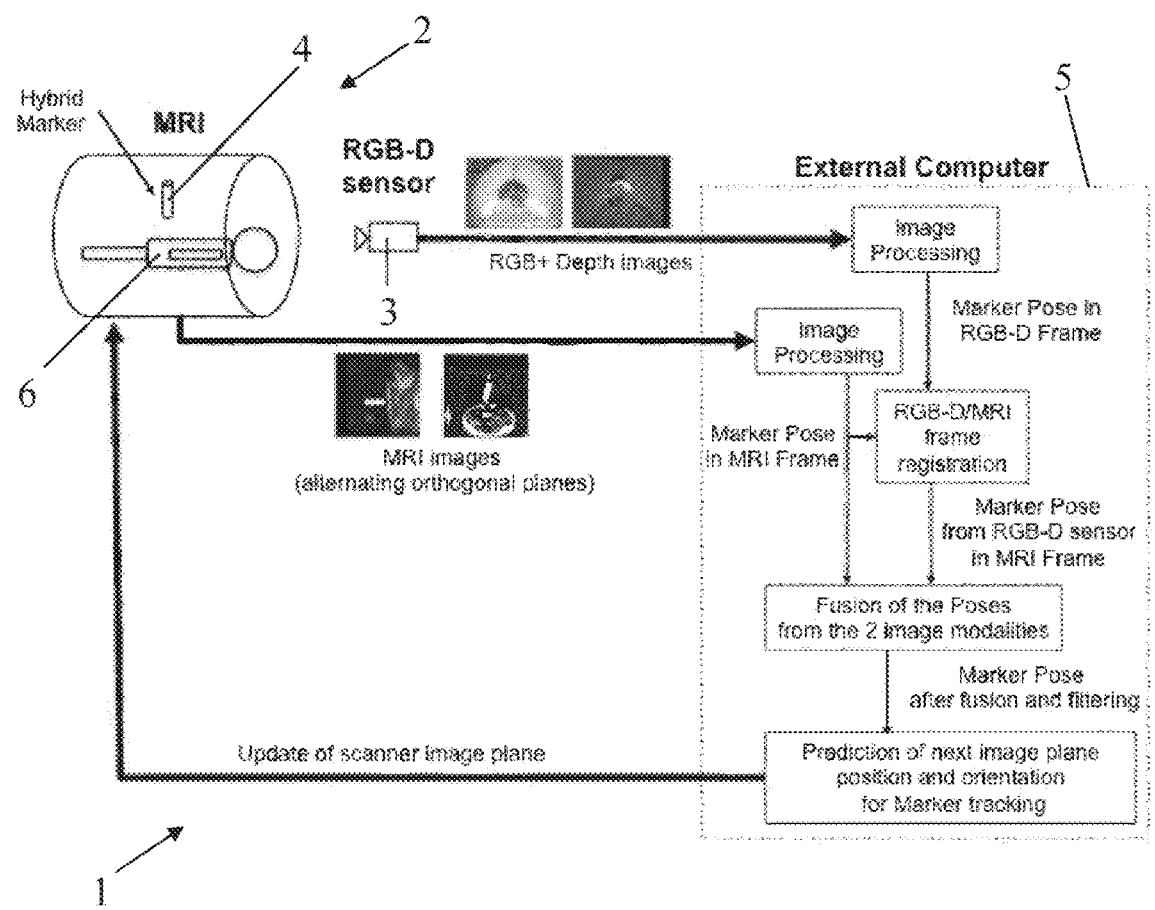

FIG. 7 is a schematic representation of the hardware components of the preferred embodiment of the invention: a RGB-D sensor as optical tracker and an external computer. The external computer receives directly the RGB-D images and the MR images through the MRI console. After processing, the predicted image plane orientation and position are sent to the MRI console for acquisition of the following MR image;

FIG. 8 is a more detailed view of the inventive system shown on FIG. 7, also illustrating the signal and data transmissions and treatment and the implemented method steps (as shown on FIGS. 1 and 2).

FIGS. 2, 7 and 8 show a system 1 according to the invention, comprising:
- an MRI scanner 2,
- an MRI multi-plane pulse sequence generating means allowing to interactively modify the position and orientation of one or several image planes in real-time,
- one or several external optical sensors 3 with high frame rate, preferably a RGB-D sensor or an other similar camera system like a stereovision systems,
- a multimodal marker 4 comprising at least one MR visible feature and one visual feature able to be tracked by both the MRI scanner 2 and the at least one external optical sensor 3,
- a computer 5 able to process in real-time the images from both MRI and optical sensor in order to fuse the detected marker position and orientation or pose from both modalities, and predict or estimate the next image plane position and orientation based on the estimated motion of the moving marker 4, in order to automatically track said marker 4 and automatically align the image planes with respect to the marker 4, or to the holding system or body location it is fixed on.

The clinical MR imaging sequence that is used during the procedure (scanning, medical intervention, motion tracking) allows to sequentially acquire MR image planes and to change interactively their individual position and orientation. In the preferred embodiment, the MRI marker is directly detected in the clinically used MR images, thus there is not need for additional MRI acquisitions specifically for tracking the marker.

In the context of medical interventions, the instrument, such as a surgical needle, has normally an elongated body, rigid or not, and the marker can be fastened at any specific known location along said body, but preferably near the tip or the end portion of said body, and in any case on a known part of or position along the instrument which is to be located inside the patient during the procedure.

For MR-guided percutaneous interventions, the presented invention can be used mounted on an interventional instrument, in order to automatically align at least two image planes to the main axis of the medical instrument. Typically, two image planes are acquired orthogonal to each other, in order to monitor in real-time the needle advancement inside the patient's body. This set up allows depicting the needle path and the surrounding tissues in a "3D-like" manner. This setup also allows to obtain the full 3D pose of the marker with precise spatial information in all directions, one slice providing the missing information on the marker pose in the direction perpendicular to the other image plane.

Alternatively, the image planes of the real-time pulse sequence are also sequentially displaced in order to scan the surrounding anatomy during needle advancement.

As mentioned before, the system and method of the presented invention can be implemented with a stand-alone hybrid marker, in a similar fashion as an ultra sound imaging probe, in order to scan the anatomy with one or several imaging planes aligned with respect to the marker.

Usually, at the beginning of the MR-guided percutaneous procedure, the medical instrument path, from the entry point on the patient skin to the targeted area, is defined by the physician. Typically, this entry point and the adequate path angulation are defined by interactively aligning one or several image planes to the main axis of an MR-visible object.

In this preliminary preparatory phase, the present invention can be implemented with a stand-alone hybrid marker, containing an ink pen or other skin marking device. After an interactive search for the adequate instrument path (entry point and orientation), the entry point could be traced on the patient's skin.

Alternatively in interventional or conventional diagnostic MRI, as well as for patient scanning, the hybrid marker could be used stand-alone, mounted on the patient body, either glued or maintained in contact with the patient body with another holding system (for instance a compliant arm). The presented invention can be used to track physiological (e.g. respiration), voluntary (e.g. limb motion) or unvoluntary (e.g. tremor or patient table motion) patient motion, for instance to stabilize the image acquisition with regards to a given anatomical feature.

The hybrid marker used for tracking has to be detected in both the MR images and in the RGB-D sensor images for the hybrid tracking.

Figure 4:
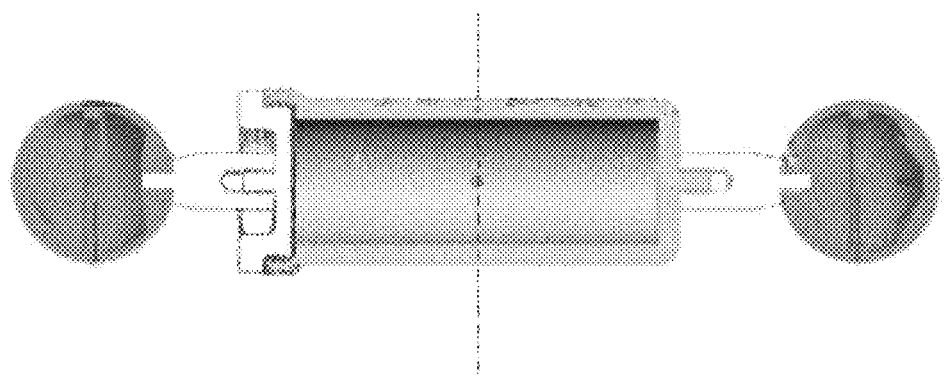
FIG. 4 is a sectional view of an example for a multimodal marker compatible with the invention. The central and cylindrical body is filled with an MRI visible material and the optical sensor detects the 2 spherical and colored features located at the distal ends of the marker.

In one embodiment, a cylindrical marker (FIG. 4) filled with an MR contrast agent/water solution (Gd-DTPA 5 mM) and with two colored spherical features attached at its distal ends is used. The MR contrast agent solution and the colored spherical features are well detectable in MR images and RGB images from the RGB-D sensor, respectively. The MR and optical features have a joint main axis, referred in the following as the hybrid marker main axis.

For tracking of the marker pose (orientation and position) in the MR images alone, clinically usable real-time image planes are used during the real-time tracking. In the preferred embodiment, two simple oblique image planes, orthogonal to each other, are aligned to the marker main axis. The tracking procedure typically starts with the acquisition of a simple oblique sagittal plane (Image 1, FIG. 6a). The passive marker is then detected in Image 1, its 3D pose (Pose 1) is computed and the corresponding pose of a new simple oblique transversal image plane (Image 2, FIG. 6*b*) aligned with the marker is calculated. After acquisition of Image 2, the current pose (Pose 2) of the passive marker is again detected in the image in order to update position and orientation of a new sagittal oblique image plane (Image 3).

From then on, the acquisition alternates between the two orthogonal image planes: typically a sagittal (odd image numbers) and a transversal plane (even image numbers). The detected marker main axis in one of the two image planes is used to update the position and orientation of the following image plane according to the MR feature detection (FIG. 2 with a disabled optical sensor).

These images typically depict the marker held by the physician over the patient's body (FIG. 6). The detection algorithm has thus to be robust against potentially segmented anatomical structures of the patient's body or of the physician's body holding the marker. For that matter, the first step of the detection algorithm is the image segmentation.

A threshold is determined in order to separate image foreground and background. Foreground of the image consists in the patient's body, the marker and the anatomical structures of the person holding the marker.

After labelling of the segmented objects, their geometrical properties, such as position, intensity weighted position and mean intensity, are determined. Further geometrical properties are determined using an ellipse-fitting algorithm calculating orientation, axes length and eccentricity of the ellipses fitted to the segmented objects (cf. "A label geometry image filter for multiple object measurement". D. Padfield and J. Miller. The Insight Journal, http://hdl.handle.net/1926/1493, 2008).

The classification of objects is then achieved with a score system based on the previously determined geometrical features. According to their global score, objects are classified as marker (only one is expected) or non-marker objects. The global score is calculated for every segmented object based on its sub-scores for size (A), intensity (B) and eccentricity (C). The global score is the weighted sum of the previously calculated scores: $S(i)=0.6.A(i)+0.3 B(i)+0.6 C(i)$.

According to its global score, an object is classified as 'marker' if its score is above a defined threshold. If more than one object is classified as 'marker', only the highest score is retained as the marker.

Figure 3:
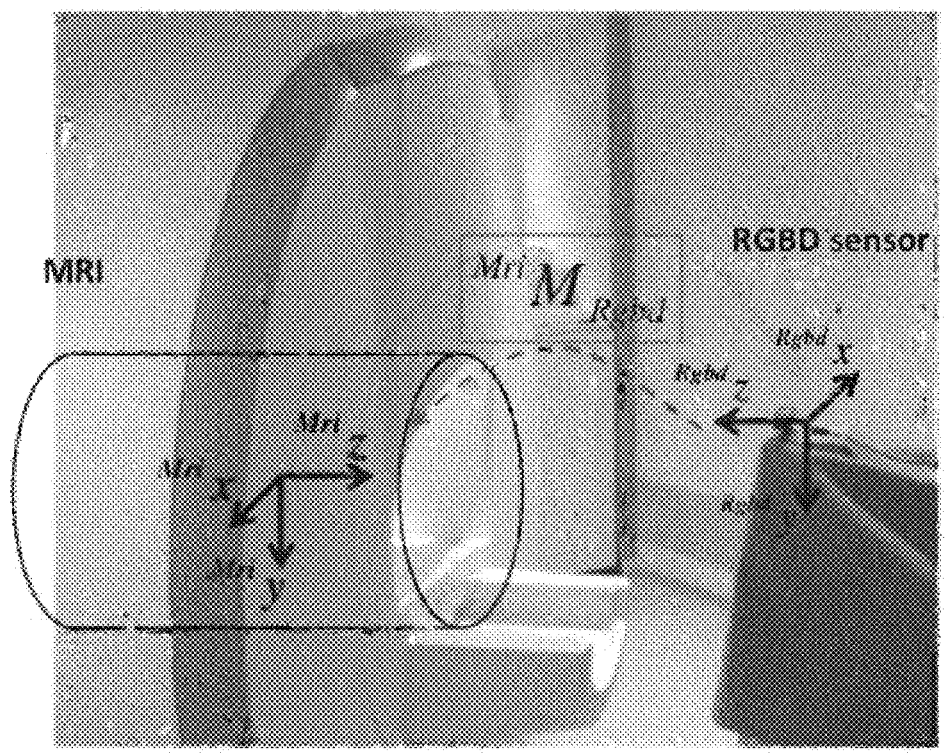
FIG. 3 is an image view illustrating the rigid transformation, i.e. translation and rotation, $^{MRI}M_{RGB-D}$ between the MRI spatial coordinate system and the optical sensor spatial coordinate system.

The 3D pose of the marker in the MRI frame (defined in FIG. 3) is then defined by $x_{pose}=(x, y, z, \alpha, \beta, \gamma)^T$ with $(x, y, z)^T$ the position of the marker center and $(\alpha, \beta, \gamma)^T$ the roll-pitch-yaw orientation angles of the marker main axis.

From this pose, the pose of the next orthogonal image plane is computed and send to the MRI scanner.

However, pure tracking in the MRI scanner suffers from a slow temporal acquisition rate, around 1 image per seconds, of thin image slices, (slice thickness typically on the order of 5 mm), leading to frequent loss of the passive marker in the image with fast motion during fast marker motion.

In accordance with the invention, the MRI based passive tracking is augmented with an optical tracking, providing a perspective projection measurement and a high temporal frequency acquisition rate to compensate for pure MRI tracking drawbacks. As an external tracker requires registration with the MRI frame, an automatic and online registration is proposed based on their simultaneous respective marker pose measurements.

In the preferred embodiment of the invention, a RGB-D (Red Green Blue-Depth) sensor is used as optical tracker. An RGB-D sensor delivers RGB images and a depth image of an observed scene. It combines an RGB camera with an infrared (IR) projector and an IR camera. The IR projector and camera work together as a depth sensor: an IR speckle dot pattern is projected on a scene and the IR camera captures the reflected speckles. The projected dot pattern and the camera observed dot pattern are compared. Due to a position shift of the observed dot pattern that is a function of the distance of the object to the RGB-D sensor, it is possible to determine the depth of the object.

In order to measure the 3D pose of the marker with the RGB-D sensor, positions of the two colored features are detected in the images and their 3D positions are calculated in the RGB-D camera frame. The RGB and depth images are temporally synchronized and acquired with the higher frame rate of 30 frames per second.

Detection of the two colored features starts with the transformation of the RGB image to Hue Saturation Value (HSV) color space and the application of an experimentally determined threshold. The HSV space revealed as the most intuitive color representation.

The orientation of the marker is computed by defining a vector from the 3D position of the upper feature pointing towards the position of the lower feature. The 3D marker position is defined as the middle position between the two detected features. However, expressed in the RGB-D sensor, this marker pose requires to be transformed in the MRI spatial coordinate system in order to align the image planes on the marker.

Registration consists in the determination of a geometrical relationship between two spatial coordinate systems using a transformation.

An online registration consists in finding and updating the transformation $^{MRI}M_{RGB-D}$ between the MRI frame and the RGB-D sensor frame online during the intervention (FIG. 1). The simultaneous acquisitions of the marker pose in both modalities enable the online and automatic registration of the system during the procedure, i.e. the estimation of the rigid transformation between the MRI frame and the vision sensor frame, enabling data fusion and preventing a manual registration procedure.

In the beginning of the tracking procedure, the registration between the MRI frame and the optical sensor spatial coordinate system is unknown. During the automatic online registration step, the instrument tracking is performed using MRI measurements only (directly in the MRI frame). At the beginning of the intervention, a number of matched points (at least three) is acquired in both the MRI frame and the RGB-D sensor frame in order to determine the 3D rigid transformation between the point sets. In our case, a pair of matched points is composed of the marker center coordinates in both modalities and detected during the same RGB-D acquisition period. After successful automatic online registration, the instrument tracking is performed using combined data from both modalities.

An advantage of the chosen approach is that the point sets in both frames are extended and updated during the entire intervention allowing to improve and refine the registration accuracy over time. In addition, the continuous online registration allows to change the position of the RGB-D sensor at any time during a procedure, for instance in order to achieve an optimal line-of-sight between the optical sensor and optical marker inside the MRI scanner. The position and orientation of the optical sensor with respect to the MRI scanner could also unwillingly change during the image-guided procedure, or it could be altered for practical access reasons to the patient or to a given area in the room.

In such cases, change in the relative position and orientation of one sensor to the other is detected by monitoring of the distance between corresponding points. If the euclidien distance between the last set of acquired corresponding points goes above a threshold with the current registration, i.e. current rigid transformation between the 2 frames of reference, a change in the pose of one sensor is assumed. Consequently, the online registration is automatically reset, and started over.

In "Vision par ordinateur: outils fondamentaux". R. Horaud and O. Monga. Hermès, 2nde édition, May 2011, the registration problem is presented as the search for an optimal correspondence transformation (rotation $^{MRI}R_{RGB\text{-}D}$ and translation $^{MRI}T_{RGB\text{-}D}$) between two 3D point clouds describing the same observations but acquired in different frames. This method for determination of the optimal rotation is based on a work for robot hand/eye registration, presented in "A new technique for fully autonomous and efficient 3Drobotics hand/eye calibration". R. Y. Tsai and R. K. Lenz. IEEE Transactions on Robotics and Automation, 5(3):345-358, 1989. They underline that this method has a singular case for a rotation of $\pm\pi$ around one rotation axis.

For this reason and in order to use this approach regardless of its singular case, an avoidance mechanism is implemented in the embodiment of the invention. If the approximate rotation angle is near $\pm\pi$, the marker positions in frame $F_{RGB\text{-}D}$ are represented in an intermediate frame $F_I$ allowing to avoid the singularity. The rotation according to the method here above is then calculated between $F_{MRI}$ and $F_I$. The final rotation between $F_{MRI}$ and $F_{RGB\text{-}D}$ can then be derived.

The approximate solution to the registration problem is based on the definition of a frame Feig that is linked to the 2 point clouds in MRI and RGB-D frames. Three non-aligned matched points are used for definition of this frame with the vectors $$u_{RGB-D} = \frac{O_1O_2}{|O_1O_2|},\ w_{RGB-D} = \frac{O_1O_3}{|O_1O_3|},\ v_{RGB-D} = w_{RGB-D} \times u_{RGB-D}$$

$$u_{MRI} = \frac{O_1O_2}{|O_1O_2|},\ w_{MRI} = \frac{O_1O_3}{|O_1O_3|},\ v_{MRI} = w_{MRI} \times u_{MRI}$$

The rotation matrices $^{RGB\text{-}D}R_{eig}=[u_{RGB\text{-}D},\ v_{RGB\text{-}D},\ w_{RGB\text{-}D}]$ and $^{MRI}R_{eig}=[u_{MRI},\ v_{MRI},\ w_{MRI}]$ represent the rotation between Feig and the frames $F_{RGB\text{-}D}$ and $F_{MRI}$ respectively. The approximate rotation matrix between the frames $F_{MRI}$ and $F_{RGB\text{-}D}$ can thus be calculated with $$^{MRI}R_{RGB\text{-}D\_approx}=^{MRI}R_{eig}(^{RGB\text{-}D}R_{eig})^T$$

One can notice that this method is referred to as approximate as it relies only on three matched points instead of all the available points and is thus highly sensitive to measurement errors on the chosen points. If the rotation angle in the axis-angle representation of the rotation matrix is $^{MRI}R_{RGB\text{-}D\_approx}$ within 0.2 radian near $\pm\pi$ the aforementioned method is near its exceptional case. In order to avoid the singularity, the point cloud of RGB-D marker position is represented in an intermediate frame $F_I$, rotated by $-\pi$ around the approximate rotation axis. For this purpose the approximate rotation axis is multiplied by $\pi$ and then converted to the rotation matrix $^I R_{RGB\text{-}D}$. The marker position clouds O in RGB-D frame are then represented in the frame FI with $$^IO=^IR_{RGB\text{-}D}O.$$

The rotation matrix $^{MRI}R_I$ is then searched between the marker positions clouds C and $^IO$ according to the previously quoted Horaud and Monga publication. Eventually, the final rotation matrix between the point clouds C and O can be calculated by accounting for the intermediate frame in the following manner:

$$^{MRI}R_{RGB\text{-}D}=^{MRI}R_I\ ^IR_{RGB\text{-}D}$$

The translation $^{MRI}T_{RGB\text{-}D}$ between the two frames is then obtained from the previously quoted Horaud and Monga publication with the previously estimated rotation.

Continuous update of the registration is then achieved by updating the point list of matched points between the 2 frames used in the estimation of the transformation $^{MRI}M_{RGB\text{-}D}$ described above.

New matching points are verified with respect to their distance to the MRI isocentre and the distance to the other points in the list. If the list is already full, it is tested if the new point would improve spatial distribution of the point list. If so, an existing point in the list will be replaced by the arriving point.

As soon as enough matching points are available and a frame transformation is estimated, pose measurements of the RGB-D sensor can be expressed in the MRI frame and used for tracking.

During the online registration (beginning of the procedure or motion of the optical sensor relative to the MRI scanner), the MR feature tracking measurement alone is available and used for marker tracking. In such case, if there is no current knowledge on the marker position and orientation (beginning of the procedure or marker loss), an MR tracking initialization step is necessary. This step consists in acquiring a dedicated, typically transversal, projection image (FIG. 6a) at the MRI scanner isocentre, or centered on the last known marker position. This projection image has a large slice thickness (typically 100 to 600 mm) compared to clinical real-time MR-guidance images (typically 5 mm). The image dimension and its slice thickness provide an initial search volume within the MRI-scanner. The MR feature and all anatomical structures of the patient lying within this volume are thus superimposed in a single projection image in said volume. As a consequence, these projection acquisitions are typically not clinically usable, and therefore referred to as "dedicated" image acquisition. The MR feature is detected in the projection image in a similar fashion as in the real-time clinical images, and its position and orientation are calculated.

Prediction of the marker pose for image plane alignment according to available measurements is then efficiently achieved with data fusion in an information filter (FIG. 1).

The information filter is a formulation of the Kalman filter that uses information measurements to represent the states of the system. The implementation of the Information filter proposed in "A formally verified modular decentralized robot control system". A. G. O. Mutambara and H. F. Durrant-Whyte. In Proceedings of the 1993 IEEE/RSJ International Conference on Intelligent Robots and Systems '93, IROS '93, volume 3, pages 2023-2030 vol. 3, 1993, and in "Decentralized Estimation and Control for Multisensor Systems". A. G. O. Mutambara. CRC Press Inc, January 1998 is used in the preferred embodiment of the invention.

One common model used with tracking is the constant velocity assumption. The motion model is then given by $$x(k)=A \cdot x(k-1)+n(k-1)$$

with $$x(k) = \begin{bmatrix} x_{pose}(k) \\ \dot{x}_{pose}(k) \end{bmatrix},$$

the marker pose (position and orientation) and its derivative states
and $$A = \begin{bmatrix} I & \delta t \cdot I \\ 0 & I \end{bmatrix},$$

the transition matrix with δt the sampling time of the optical sensor and n(k) a white noise.

As the marker pose is directly measured in both the MR and RGB-D images, their observation matrices in the measurement equation are equal:

$$H=H_{MRI}=H_{RGB-D}=[I\ 0]$$

$$z(k)=H \cdot x(k)+m(k)$$

The white noises on measurements $m_{RGB-D}(k)$ and $m_{MRI}(k)$ have respectively a noise covariance matrix denoted $Q_{MRI}$ and $Q_{RGB-D}$.

Therefore, if ŷ is the information state of the filter and is defined by $\hat{y}=Y\hat{x}$ with Y the information matrix, then its estimate at current time sample k is given by:

$$Y(k|k)=Y(k|k-1)+I_{RGB-D}(k)+I_{MRI}(k)$$

$$Y(k|k)=Y(k|k-1)+H^T Q_{MRI}^{-1} H+H^T Q_{RGB-D} H$$

$$\hat{y}(k|k)=\hat{y}(k|k-1)+i_{MRI}+i_{RGB-D}$$

$$\hat{y}(k|k)=\hat{y}(k|k-1)+H^T Q_{MRI}^{-1} z_{MRI}+H^T Q_{RGB-D}^{-1} z_{RGB-D}$$

with the local information state contribution $i_{MRI}$, $i_{RGB-D}$ and $z_{MRI}$, $z_{RGB-D}$ the marker pose measurement respectively by the MRI and RGB-D sensors.

Figure 5:
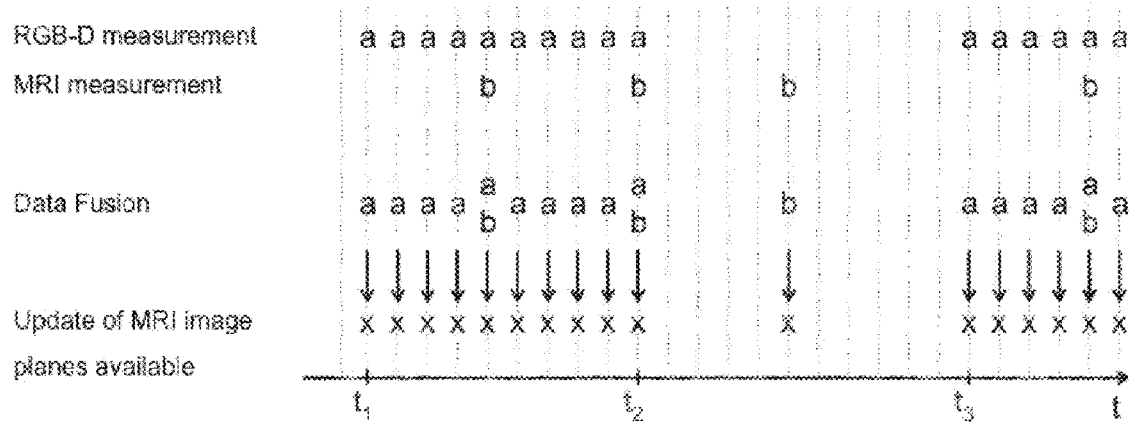
FIG. 5 is a chronogram for the fusion of MRI and RGB-D pose measurements of the marker in the preferred embodiment. If the high frame rate measurement of the RGB-D sensor is temporarily unavailable due to loss of line-of-sight, update of image planes is based only on MR images, and inversely.

If one modality measurement is not available at the current time step, its local contribution state is simply removed from the sum used for the estimation (FIG. 5). The prediction step associated with the estimation step is given by:

$$\hat{y}(k+1|k)=L(k+1|k)\hat{y}(k|k)$$

$$Y(k+1|k)=[A\ Y^{-1}(k|k)A^T+Q(k+1)]^{-1}$$

with $$L(k+1|k)=Y(k+1|k)A\ Y^{-1}(k|k)$$

Prediction of the marker pose is retrieved from the information filter prediction $$\hat{x}(k+1|k)=Y^{-1}\hat{y}(k+1|k)$$

based on the constant velocity model and current available measurement (MRI/RGB-D). It is then used to compute the alignment of the image planes for the next acquisition.

The system runs periodically, with a period equal to the highest sensor acquisition framerate, i.e. optical sensor in the preferred embodiment.

More precisely, in accordance with a preferred embodiment of the invention, the method for multi-sensor tracking and online registration runs periodically the following steps 1 to 8:

Step 1 (Acquisition and image processing)

Marker pose measured respectively in the MRI frame and in the optical frame, depending on their respective frame rates.

If over the time period, matching marker poses are available from both modalities, a new pair of matched points between the two frames is recorded.

Step 2 (Online registration) If a new pair of matched points

If the pair of matched points improves the estimation of the rigid transformation between the 2 frames, it is added to the current list of matched points. If so, an optimization algorithm provides an updated estimation of the rigid transformation between the two frames based on the updated list of matched points.

Step 3 (Frame transformation) The current rigid transformation is used to translate to the MRI frame the marker pose in the optical frame, so that measured marker poses in both modalities are now expressed in the MRI frame.

Step 4 (Fusion)

A data fusion algorithm, for instance an information filter, is used to filter the available pose(s) and estimate the optimal pose of the marker considering a model of the tracking process and its noise.

Step 5 Pose Prediction using the data fusion algorithm

Step 6 Calculation of the corresponding image plane position and orientation encompassing the marker Step 7 Predicted image plane position and orientation sent to the MRI console to update the image plane acquisition.

Thus, as described before, the invention aims at automatic image plane alignment to a moving instrument in order to accelerate and improve the accuracy of medical interventions under MRI-guidance.

The presented system and methods of the invention intends to suppress the requirement for time-consuming manual alignment of the image plane to the marker or instrument pose. The presented invention also accelerates the procedure thanks to its automatic online registration, therefore not requiring a prior registration step before the procedure starts (FIGS. 1 and 8).

A hybrid marker composed of one feature visible in the MR images and visual features detected by an external optical sensor, preferably a RGB-Depth sensor, is tracked in real-time. The current pose (position + orientation) of the moving marker is measured using both MRI and optical sensors, and the MR image planes are automatically aligned to the predicted pose at the time of the following MRI acquisition. The marker can be used stand-alone for dynamic scanning of the anatomy, and can also be used in order to localize the optimal entry point and path angulation for the interventional instrument prior to the intervention. Placed on the surgical instrument, the marker enables an automatic alignment of the image planes to the instrument axis in order to obtain a "3D-like" view of the instrument path inside the patient's body towards the targeted area, and of the surrounding anatomy.

By fusion, as with an information filter, of both MRI scanner and optical sensor measurements, the pose of the marker is estimated even if one of these two modalities is not available. Pose estimation is retrieved by image processing on an external computer that accordingly drives the position and orientation of acquired MRI image planes based on the prediction.

Simultaneous tracking in both modalities enables the continuous online registration of the system, i.e. estimation of the rigid transformation between the MRI frame and the optical sensor frame. It thus automatically allows for new registration if the location of the optical sensor is changed relative to the MRI scanner during an image-guided procedure. Therefore it becomes possible to change the optical sensor position in order to achieve the best line-of-sight between the marker and the optical sensor with automatic new registration of the system.

As mentioned before, the inventive method comprises a priori image alignment with no update of the magnetic field gradients during the image acquisition time, nor adaptation of the image reconstruction to motion during the image acquisition.

The present invention is of course not limited to the preferred embodiments described and represented herein, changes can be made or equivalents used without departing from the scope of the invention.

The invention claimed is:

1. A method for tracking a moving multimodal marker, stand-alone or fixed on an instrument, on a holding system, or on a subject's body, wherein said method comprises an automatic image plane alignment process using a system (1) comprising:
   an MRI scanner (2),
   an MRI multi-plane pulse sequence generating means configured to interactively modify the position and orientation of one or more image planes in real-time,
   at least one external optical sensor (3) with high frame rate,
   a multimodal marker (4) comprising at least one MR visible feature and one visual feature configured to be tracked by both the MRI scanner (2) and the at least one external optical sensor (3),
   a computer (5) configured to process in real-time images from both the MRI scanner and the at least one external optical sensor in order to fuse a detected marker position and an orientation or a pose from both modalities, and predict or estimate a position and an orientation of a next image plane based on estimated motion of the multimodal marker (4), in order to automatically track the multimodal marker (4) and automatically align the image planes with respect to the multimodal marker (4), or to the holding system or body location the multimodal marker (4) is fixed on, said method comprising the steps of:
   processing in real-time the images from both the MRI scanner and the at least one external optical sensor in order to fuse the detected position of the multimodal marker (4) and orientation or pose from both modalities, and of predicting or estimating the next image plane position and orientation based on the estimated motion of the moving multimodal marker (4), in order to automatically track said multimodal marker (4) and automatically align the image planes with respect to the multimodal marker (4), or to the instrument or body location the multimodal marker (4) is fixed on,
   wherein with the multimodal marker being fixed on the instrument, performing a process for automatic multimodal real-time tracking of the multimodal marker (4) for image plane alignment in magnetic resonance imaging comprises the steps of:
   providing the multimodal marker (4) comprising at least one MR visible feature and at least one visual feature;
   providing a real-time interactive MRI pulse sequence configured to update of the image plane(s) position and orientation;
   providing an MRI sensor (2) for marker pose measurement in the MRI frame;
   providing the at least one external optical sensor (3) for marker pose measurement inside the MRI scanner;
   defining the system time period as the period of the at least one external optical sensor with the highest acquisition frame rate;
   (a) measuring the marker pose in the MRI frame and/or in the at least one external optical sensor frame, depending on their respective frame rates;
   (b) when a marker pose measurement is available from the at least one external optical sensor, translating the marker pose measured in the at least one external optical sensor frame to the MRI frame using the current rigid transformation between the MRI frame and the the at least one external optical sensor frame;
   (c) filtering and estimating the optimal pose of the multimodal marker considering a model of the tracking process and the multimodal marker's (4) noise, using a data fusion algorithm;
   (d) predicting the marker pose based on the optimal estimation, using a data fusion algorithm;
   (e) calculating the corresponding image plane position and orientation encompassing the multimodal marker based on the prediction of the marker pose from the data fusion algorithm;
   (f) providing the predicted image plane position and orientation to an MRI console;
   (g) updating the real-time interactive MRI pulse sequence image plane position and orientation based on the predicted image plane position and orientation;
   (h) in parallel to steps (b) to (g), following step (a), providing a new pair of matched points when matching marker poses are available from both the MRI sensor and the at least one external optical sensor over the time period;
   (i) in parallel to steps (b) to (g), following step (h), adding to the current list of matched points the new pair of matched points when adding the new pair of matched points improves the estimation of the rigid transformation between the MRI frame and the the at least one external optical sensor frame; and
   (j) in parallel to steps (b) to (g), following step (i) updating the estimation of the rigid transformation between the two frames using an optimization algorithm based on the updated list of matched points.

2. The method according to claim 1, wherein a hybrid method is used for the automatic alignment of the image planes to the multimodal marker (4) whose 3D pose can be measured by at least the MRI sensor (2) and the at least one external optical sensor (3) in the MRI scanner (2).

3. The method according to claim 1, wherein simultaneous acquisitions of the marker pose in both modalities are used in order to perform an online and automatic registration of the system during the method, including the estimation of the rigid transformation between the MRI frame and the at least one external optical sensor frame.

4. The method according to claim 3, wherein a new registration is performed automatically when the location of the at least one external optical sensor in an MRI room is changed during the method.

5. A method for scanning the anatomy of a subject, wherein said method incorporates tracking of a stand-alone hybrid marker according to the method of claim 1, the scanning being performed with one or several imaging planes aligned with respect to the multimodal marker.

6. A method for tracking subject motion during MR imaging, wherein said method incorporates tracking of a stand-alone hybrid marker, mounted on the body of the subject or maintained in contact with the body of the subject, according to the method of claim 1, in order to stabilize MR image acquisition with regards to a given anatomical feature of the subject.

7. The method according to claim 1, wherein the at least one external optical sensor (3) is a RGB-D sensor.

8. The method according to claim 1, wherein the multimodal marker (4) is a stand-alone hybrid marker configured to i) interactively locate an entry point on the skin of the subject (6) and angulation towards a targeted area of the instrument or ii) interactively scan the subject anatomy.

9. The method according to claim 1, wherein the multimodal marker (4) is a hybrid marker which is fixed on a surgical instrument (7) in order to automatically track the instrument and automatically align the image planes with respect to the instrument actual path, including the path of the tip or of an end portion of the instrument inside the subject.

10. The method according to claim 1, wherein the data fusion algorithm is an information filter that estimates the multimodal marker pose from the fusion of measurements of both tracking modalities, or from the measurement of a single or remaining tracking modalities when the pose measurement from other tracking modalities is unavailable at a current sampling time.

11. The method according to claim 1, wherein simultaneous acquisitions of the marker pose in both modalities enable online and automatic registration of the system during the method, including the estimation of the rigid transformation between the MRI frame and the at least one external optical sensor frame.

12. The method according to claim 11, wherein a new registration is automatic when the location of the at least one external optical sensor in an MRI room is changed during the method.

13. The method according to claim 1, wherein the multimodal marker contains a skin marking means in order to mark the entry point on the subject's skin.

14. The method according to claim 1, wherein the multimodal marker is mounted on the holding system.

15. The method according to claim 1, wherein the multimodal marker is mounted on the holding system configured to change, and then to maintain a chosen position and angulation of the multimodal marker inside the MRI scanner.

16. The method according to claim 1, wherein the MRI visible feature is a stereotactic marker.

17. The method according to claim 1, wherein the visual feature is a stereotactic target.

* * * * *